(12) United States Patent
Prandi et al.

(10) Patent No.: US 9,168,074 B2
(45) Date of Patent: *Oct. 27, 2015

(54) RESORPTIVE INTRAMEDULLARY IMPLANT BETWEEN TWO BONES OR TWO BONE FRAGMENTS

(71) Applicant: MEMOMETAL TECHNOLOGIES, Bruz (FR)

(72) Inventors: Bernard Prandi, Rennes (FR); Marc Augoyard, Tassin la Demi Lune (FR); Thomas Ledermann, Eschenbach (CH); Tristan Meusnier, Saint-Etienne (FR); Jacques Peyrot, Tassin la Demi Lune (FR); Judith Fellmann, Stafa (CH)

(73) Assignee: MEMOMETAL TECHNOLOGIES (FR)

( * ) Notice: Subject to any disclaimer, the term of this patent is extended or adjusted under 35 U.S.C. 154(b) by 114 days.

This patent is subject to a terminal disclaimer.

(21) Appl. No.: 13/795,946

(22) Filed: Mar. 12, 2013

(65) Prior Publication Data

US 2013/0190761 A1    Jul. 25, 2013

Related U.S. Application Data

(63) Continuation of application No. 12/918,105, filed as application No. PCT/FR2009/051658 on Sep. 2, 2009, now Pat. No. 8,414,583.

(30) Foreign Application Priority Data

Sep. 9, 2008    (FR) ...................................... 08 56035

(51) Int. Cl.
*A61B 17/72* (2006.01)
*A61B 17/68* (2006.01)
(Continued)

(52) U.S. Cl.
CPC ............. *A61B 17/7233* (2013.01); *A61B 17/68* (2013.01); *A61F 2/4225* (2013.01);
(Continued)

(58) Field of Classification Search
CPC ....................... A61B 17/7208; A61B 17/7266
USPC ...................................................... 606/62–64
See application file for complete search history.

(56) References Cited

U.S. PATENT DOCUMENTS 3,462,765 A    8/1969   Swanson
3,466,669 A    9/1969   Flatt
(Continued)

FOREIGN PATENT DOCUMENTS

CA    2836654 A1    6/2014
CA    2837497 A1    6/2014
(Continued)

OTHER PUBLICATIONS

International Search Report for PCT/FR2008/050453 dated Nov. 4, 2008.
(Continued)

*Primary Examiner* — Ellen C Hammond
(74) *Attorney, Agent, or Firm* — Lerner, David, Littenberg, Krumholz & Mentlik, LLP

(57) ABSTRACT

The invention relates to an intramedullary implant for use between two bones or two bone fragments. The implant includes a single-piece body having a generally elongate shape and having, at each end, areas for anchoring to the bone portions in question, characterized in that one of said areas has a generally cylindrical shape while the other area has a flat cross-section.

18 Claims, 4 Drawing Sheets

Figure 1:
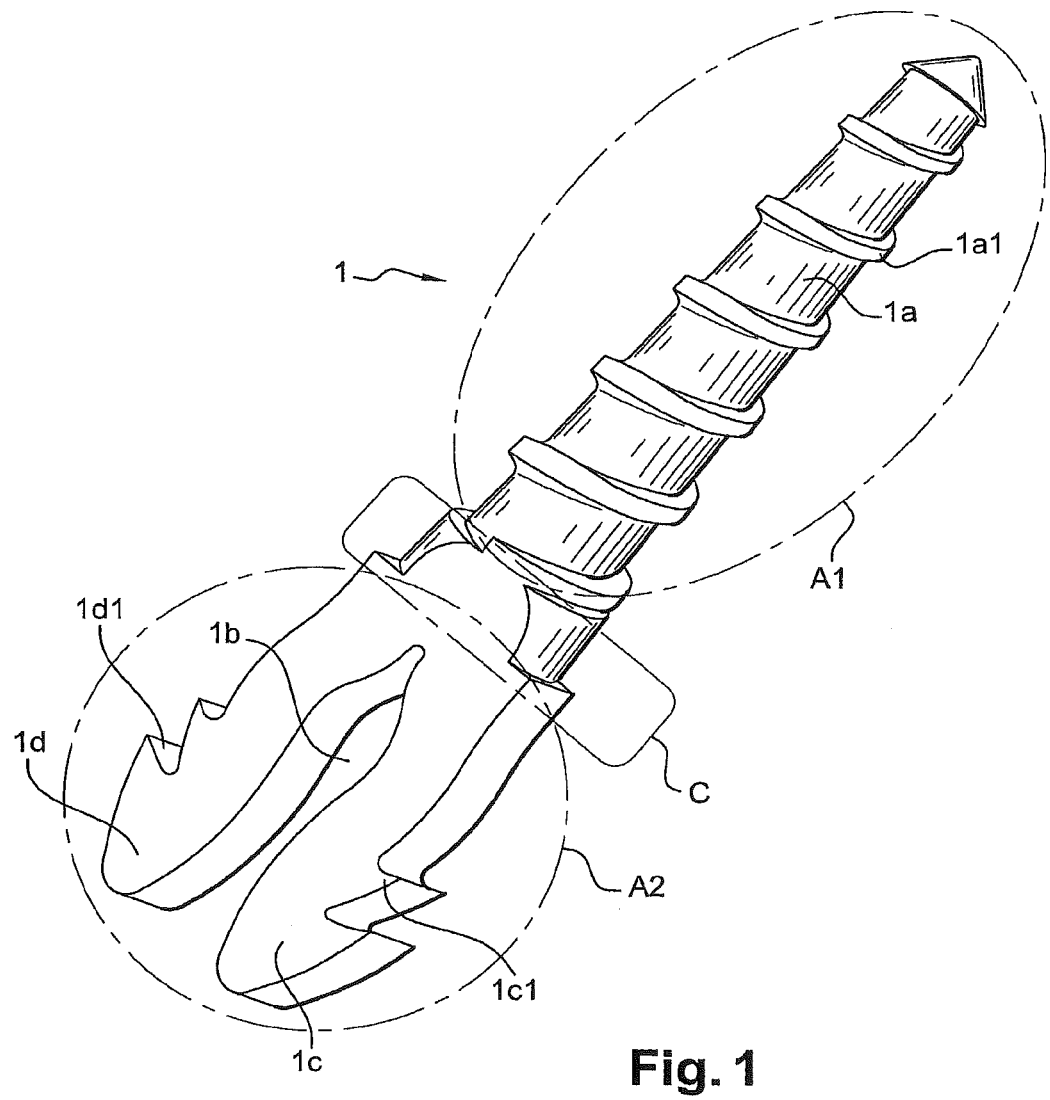

(51) Int. Cl.
*A61F 2/42* (2006.01)
*A61B 17/86* (2006.01)
*A61F 2/30* (2006.01)

(52) U.S. Cl.
CPC ........... *A61F2/4241* (2013.01); *A61B 17/7208* (2013.01); *A61B 17/7225* (2013.01); *A61B 17/7266* (2013.01); *A61B 17/7283* (2013.01); *A61B 17/8605* (2013.01); *A61F 2002/30062* (2013.01); *A61F 2002/3085* (2013.01); *A61F 2002/30563* (2013.01); *A61F 2002/30622* (2013.01); *A61F 2002/30878* (2013.01); *A61F 2210/0004* (2013.01)

(56) References Cited

U.S. PATENT DOCUMENTS

| | | |
|---|---|---|
| 3,593,342 A | 7/1971 | Niebauer et al. |
| 3,681,786 A | 8/1972 | Lynch |
| 3,739,403 A | 6/1973 | Nicolle |
| 3,805,302 A | 4/1974 | Mathys |
| 3,824,631 A | 7/1974 | Burstein et al. |
| 3,875,594 A | 4/1975 | Swanson |
| D243,716 S | 3/1977 | Treace et al. |
| 4,158,893 A | 6/1979 | Swanson |
| 4,204,284 A | 5/1980 | Koeneman |
| 4,276,660 A | 7/1981 | Laure |
| 4,364,382 A | 12/1982 | Mennen |
| 4,367,562 A | 1/1983 | Gauthier et al. |
| D277,509 S | 2/1985 | Lawrence et al. |
| D277,784 S | 2/1985 | Sgarlato et al. |
| 4,522,200 A | 6/1985 | Stednitz |
| D284,099 S | 6/1986 | Laporta et al. |
| 4,634,382 A | 1/1987 | Kusano et al. |
| D291,731 S | 9/1987 | Aikins |
| 4,759,768 A | 7/1988 | Hermann et al. |
| 4,871,367 A | 10/1989 | Christensen et al. |
| 4,955,916 A | 9/1990 | Carignan et al. |
| 4,969,909 A | 11/1990 | Barouk |
| 5,011,497 A | 4/1991 | Persson et al. |
| 5,047,059 A | 9/1991 | Saffar |
| 5,062,851 A | 11/1991 | Branemark |
| 5,092,896 A | 3/1992 | Meuli et al. |
| 5,108,443 A | 4/1992 | Branemark |
| 5,133,761 A | 7/1992 | Krouskop |
| 5,179,915 A | 1/1993 | Cohen et al. |
| 5,190,546 A | 3/1993 | Jervis |
| 5,207,712 A | 5/1993 | Cohen |
| 5,326,364 A | 7/1994 | Clift, Jr. et al. |
| 5,405,400 A | 4/1995 | Linscheid et al. |
| 5,405,401 A | 4/1995 | Lippincott, III et al. |
| 5,425,776 A | 6/1995 | Cohen |
| 5,425,777 A | 6/1995 | Sarkisian et al. |
| 5,480,447 A | 1/1996 | Skiba |
| 5,484,443 A | 1/1996 | Pascarella et al. |
| 5,507,822 A | 4/1996 | Bouchon et al. |
| 5,522,903 A | 6/1996 | Sokolow et al. |
| 5,554,157 A | 9/1996 | Errico et al. |
| 5,634,925 A | 6/1997 | Urbanski |
| 5,674,297 A | 10/1997 | Lane et al. |
| 5,702,472 A | 12/1997 | Huebner |
| 5,725,585 A | 3/1998 | Zobel |
| 5,782,927 A | 7/1998 | Klawitter et al. |
| 5,824,095 A | 10/1998 | Di Maio, Jr. et al. |
| 5,876,434 A | 3/1999 | Flomenblit et al. |
| 5,882,444 A | 3/1999 | Flomenblit et al. |
| 5,919,193 A | 7/1999 | Slavitt |
| 5,951,288 A | 9/1999 | Sawa |
| 5,958,159 A | 9/1999 | Prandi |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,146,387 A | 11/2000 | Trott et al. |
| 6,197,037 B1 | 3/2001 | Hair |
| 6,200,330 B1 | 3/2001 | Benderev et al. |
| 6,248,109 B1 | 6/2001 | Stoffella |
| 6,319,284 B1 | 11/2001 | Rushdy et al. |
| 6,352,560 B1 | 3/2002 | Poeschmann et al. |
| 6,383,223 B1 | 5/2002 | Baehler et al. |
| 6,386,877 B1 | 5/2002 | Sutter |
| 6,423,097 B2 | 7/2002 | Rauscher |
| 6,428,634 B1 | 8/2002 | Besselink et al. |
| 6,454,808 B1 | 9/2002 | Masada |
| 6,475,242 B1 | 11/2002 | Bramlet |
| 6,689,169 B2 | 2/2004 | Harris |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,811,568 B2 | 11/2004 | Minamikawa |
| 6,869,449 B2 | 3/2005 | Ball et al. |
| 7,037,342 B2 | 5/2006 | Nilsson et al. |
| 7,041,106 B1* | 5/2006 | Carver et al. ................. 606/309 |
| 7,182,787 B2 | 2/2007 | Hassler et al. |
| 7,240,677 B2 | 7/2007 | Fox |
| 7,291,175 B1 | 11/2007 | Gordon |
| 7,588,603 B2 | 9/2009 | Leonard |
| 7,780,737 B2 | 8/2010 | Bonnard et al. |
| 7,837,738 B2 | 11/2010 | Reigstad et al. |
| 7,842,091 B2 | 11/2010 | Johnstone et al. |
| 7,955,388 B2 | 6/2011 | Jensen et al. |
| 8,100,983 B2 | 1/2012 | Schulte |
| 8,262,712 B2 | 9/2012 | Coilard-Lavirotte et al. |
| 8,394,097 B2* | 3/2013 | Peyrot et al. ................... 606/62 |
| 8,414,583 B2 | 4/2013 | Prandi et al. |
| 8,475,456 B2 | 7/2013 | Augoyard et al. |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 2001/0025199 A1 | 9/2001 | Rauscher |
| 2002/0019636 A1 | 2/2002 | Ogilvie et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0082705 A1 | 6/2002 | Bouman et al. |
| 2003/0040805 A1 | 2/2003 | Minamikawa |
| 2003/0069645 A1 | 4/2003 | Ball et al. |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0220678 A1 | 11/2004 | Chow et al. |
| 2005/0119757 A1 | 6/2005 | Hassler et al. |
| 2005/0251265 A1 | 11/2005 | Calandruccio et al. |
| 2005/0283159 A1 | 12/2005 | Amara |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0185584 A1 | 8/2007 | Kaufmann et al. |
| 2007/0213831 A1 | 9/2007 | de Cubber |
| 2007/0239158 A1 | 10/2007 | Trieu et al. |
| 2008/0039949 A1 | 2/2008 | Meesenburg et al. |
| 2008/0132894 A1 | 6/2008 | Coilard-Lavirotte et al. |
| 2008/0154385 A1 | 6/2008 | Trail et al. |
| 2008/0177262 A1 | 7/2008 | Augoyard et al. |
| 2008/0195219 A1 | 8/2008 | Wiley et al. |
| 2008/0221697 A1 | 9/2008 | Graser |
| 2008/0221698 A1 | 9/2008 | Berger |
| 2008/0269908 A1 | 10/2008 | Warburton |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1* | 5/2010 | Peyrot et al. ................. 606/300 |
| 2010/0131072 A1 | 5/2010 | Schulte |
| 2010/0161068 A1 | 6/2010 | Lindner et al. |
| 2010/0185295 A1 | 7/2010 | Emmanuel |

(56) References Cited

U.S. PATENT DOCUMENTS

| | | |
|---|---|---|
| 2010/0249942 A1 | 9/2010 | Goswami et al. |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0301652 A1 | 12/2011 | Reed et al. |
| 2012/0065692 A1 | 3/2012 | Champagne et al. |
| 2013/0053975 A1 | 2/2013 | Reed et al. |
| 2013/0060295 A1 | 3/2013 | Reed et al. |
| 2013/0066435 A1 | 3/2013 | Averous et al. |
| 2013/0131822 A1 | 5/2013 | Lewis et al. |
| 2013/0150965 A1 | 6/2013 | Taylor et al. |
| 2014/0058462 A1 | 2/2014 | Reed et al. |
| 2014/0142715 A1 | 5/2014 | McCormick |
| 2014/0180428 A1 | 6/2014 | McCormick |
| 2014/0188239 A1 | 7/2014 | Cummings |

FOREIGN PATENT DOCUMENTS

| | | | |
|---|---|---|---|
| EP | 0420794 A1 | 4/1991 | |
| EP | 1300122 A2 | 4/2003 | |
| EP | 1923012 A1 | 5/2008 | |
| FR | 2725126 A1 | 4/1996 | |
| FR | 2783702 A1 | 3/2000 | |
| FR | 2787313 A1 | 6/2000 | |
| FR | 2794019 A1 | 12/2000 | |
| FR | 2801189 A1 | 5/2001 | |
| FR | 2846545 A | 5/2004 | |
| FR | 2846545 A1 | 5/2004 | |
| FR | 2884406 | 10/2006 | |
| GB | 2119655 A | 11/1983 | |
| GB | 2430625 A | 4/2007 | |
| GB | 2430625 B | 4/2007 | |
| JP | 60145133 | 7/1985 | |
| JP | 03-001854 A | 8/1991 | |
| JP | 7303662 A | 11/1995 | |
| JP | 2004535249 A | 11/2004 | |
| JP | 2007530194 A | 11/2007 | |
| JP | 2008188411 A | 8/2008 | |
| JP | 2008537696 A | 9/2008 | |
| WO | 9733537 A1 | 9/1997 | |
| WO | 2005063149 A1 | 7/2005 | |
| WO | 2005104961 A1 | 11/2005 | |
| WO | 2006109004 A1 | 10/2006 | |
| WO | WO 2006109004 A1 * | 10/2006 | |
| WO | 2008057404 A2 | 5/2008 | |
| WO | WO 2008129214 A2 * | 10/2008 | |
| WO | 2009103085 A1 | 8/2009 | |
| WO | 2011130229 A1 | 10/2011 | |

OTHER PUBLICATIONS

International Search Report, PCT/FR2006/050345, dated Aug. 30, 2006.

Japanese Office Action for Application No. 2011-526540 dated Aug. 13, 2013.

* cited by examiner

RESORPTIVE INTRAMEDULLARY IMPLANT BETWEEN TWO BONES OR TWO BONE FRAGMENTS

The invention relates to the technical field of orthopedic implants, particularly for arthrodesis and osteosynthesis.

More particularly, the invention relates to an intramedullary implant for arthrodesis between two bone parts or osteosynthesis between two bone fragments, particularly in the case of the hand or foot.

Different solutions have been proposed to achieve these functions.

For example, a solution comes from the teaching of patent application FR 2,884,406, of which the applicant of the present application is also the applicant. This patent describes an intramedullary osteosynthesis device made up of an elongated body whose ends constitute anchor zones cooperating with the bone parts to be immobilized. The anchor zones are shaped and made of a material selected to enable insertion into the bone parts, then to ensure an anchor in the bone parts by preventing any rotational movement by resisting traction and maintaining a compression force.

Another solution also comes from patent application FR 07.02003, also from the same applicant. This document describes an implant in the form of two anchor zones connected by a central zone and whose general shape is substantially inscribed in a very elongated rectangle while being substantially X-shaped, so as to form two legs in the anchor zones that are adapted to move apart by elastic or shape-memory effect.

From this design, different criteria have been established to make the implant easy to place and efficient in order to create a primary and secondary stability for the osteosynthesis or arthrodesis site.

However, these solutions are not adapted for the case of an implant made of resorptive material.

From this state of the art, the object that the invention proposes to attain is further improving the anchoring and the stability of the implant as well as its adaptation to the morphology of the implantation site when the implant is made of resorptive material.

To solve such a problem, a resorptive intramedullary implant between two bones or two bone fragments has been designed and developed; it is made up, in a known manner, of a single-piece body having a general elongated shape with, at each end, zones for anchoring to the bone parts being considered. According to the invention, one of the zones has a cylindrical shape, whereas the other zone is flat.

Advantageously, the implant is made of a resorptive material whose mechanical properties are determined to last the time necessary for the consolidation, so that the implant is resorbed after six months. For example, the implant is composed of lactic acid polymer or copolymer (PLA, PGA, etc.).

Considering the specific mechanical characteristics of resorptive materials, and to solve the given problem of improving anchoring and stability, the cylindrical cross-section is threaded and tapers in the direction of its free end.

To solve the given problem of enabling a deformation by elasticity, thus causing an expansion adapted to the geometry of the site and to the properties of the material, the flat cross-section zone has, substantially in its median portion, an opening adapted to enable elastic deformation of the zone. The opening defines at least two anchor arms.

It therefore appears that the combination of a cylindrical and threaded anchor zone and a flat-sectioned anchor zone is particularly advantageous with respect to the problem to be solved.

To solve the given problem of withstanding the shear and flexion forces that may occur in the area of the bone site, between the two anchor zones, the body has a central transition zone adapted to withstand the shear and flexion forces occurring in the area of the bone site and adapted to serve as an abutment.

From this basic design of the implant, the anchor zones are either coaxial or angularly offset by between about 1° and 30° and, advantageously, by 10°. The bend between the anchor zones is located so as to substantially correspond to an arthrodesis line of the bones being considered.

Figures 2, 3, 4:
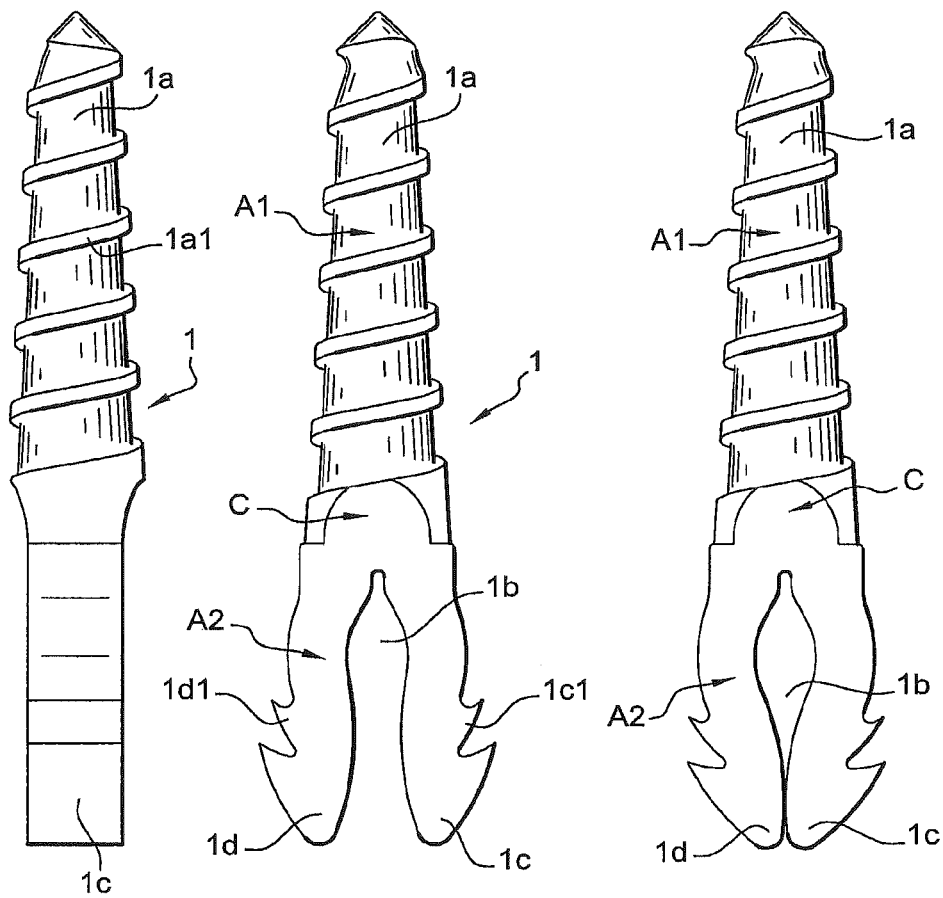
Figure 5:
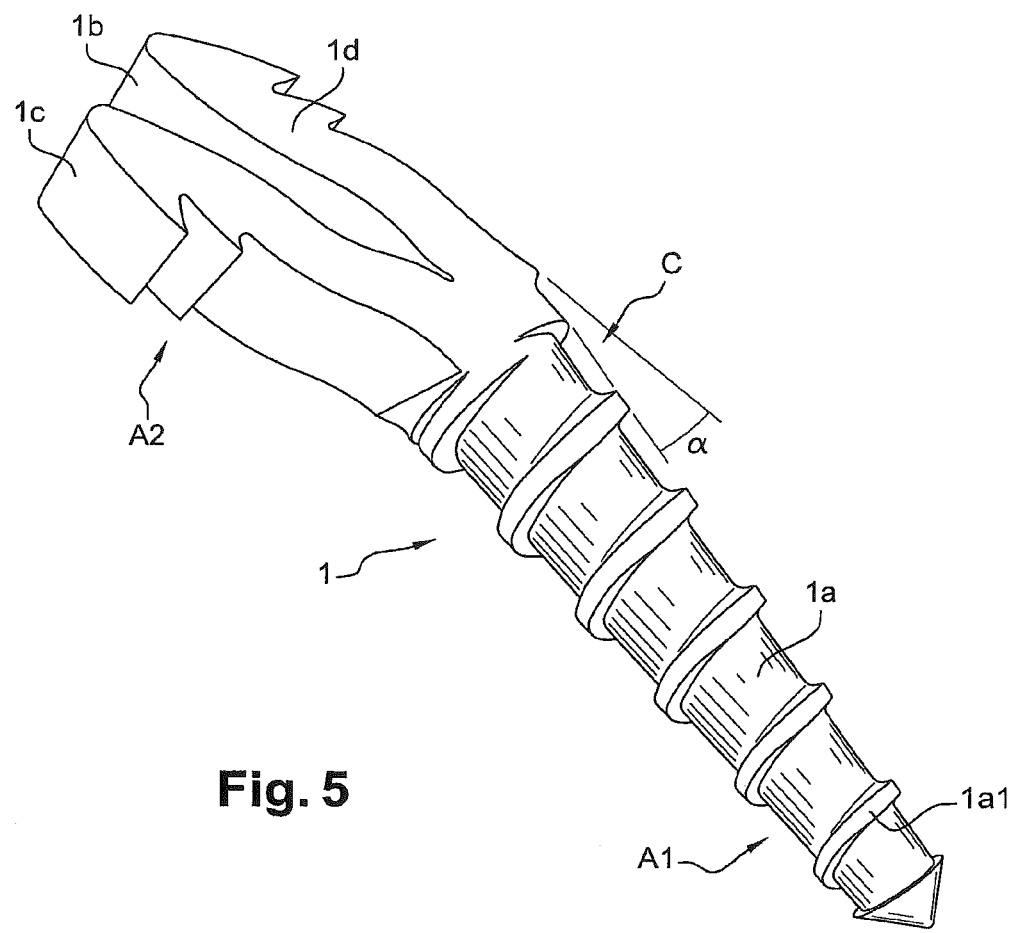
Figure 6:
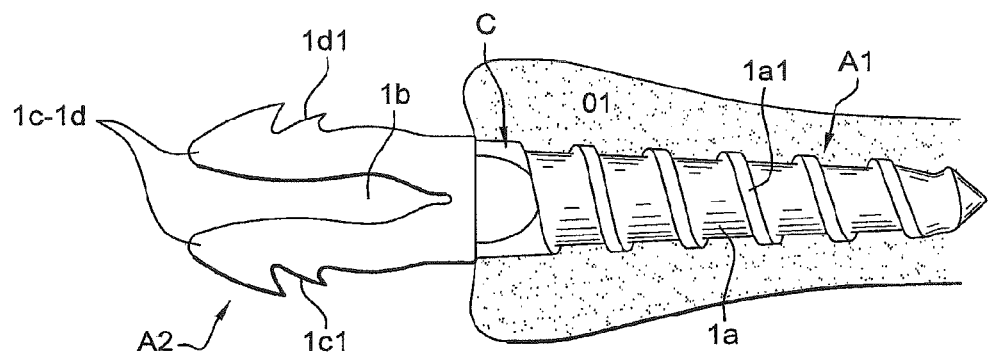
Figure 7:
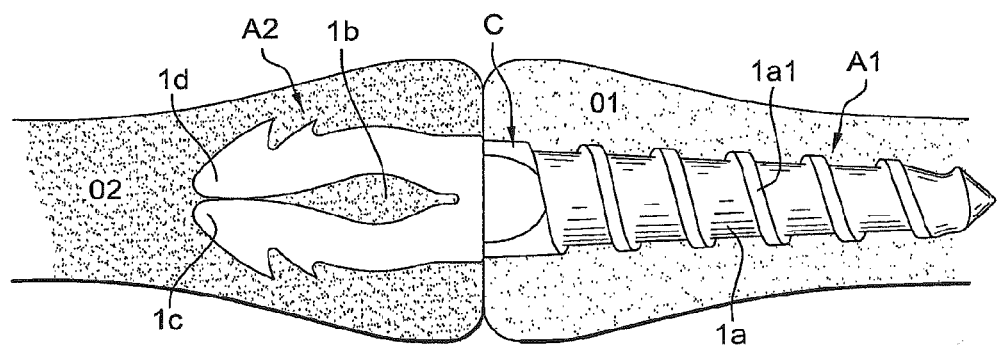

The invention is explained in more detail hereinafter with reference to the attached drawings, in which:

FIG. 1 is a perspective view of the implant;
FIG. 2 is a front view of the implant before insertion into the bone part in question;
FIG. 3 is a side view corresponding to FIG. 2;
FIG. 4 is a view like FIG. 2 showing the position of the anchor arms of the flat section after insertion;
FIG. 5 is a perspective view of another advantageous embodiment of the implant;
FIGS. 6 and 7 show the installation of the implant into two bone parts.

The implant according to the invention has a one-piece body 1 of elongated shape and having a first proximal zone A1 and a second distal zone A2. The entire implant body is made of a resorptive material whose mechanical properties are determined for the implant to be resorbed in no less than about 6 months. In one embodiment, the implant is composed of lactic acid polymer or copolymer (PLA, PGA, etc.).

As will be described later in the description, the zones A1 and A2 have anchor formations for the respective bone parts. Taking into account the specific characteristics of the resorptive material and to attain the given object of anchoring and stability, the zone A1 has a cylindrical section, whereas the other zone A2 is flat.

The zone A1 has a generally cylindrical outer surface 1a with a limited taper toward its free end. The surface 1a has a helical rib forming a screw thread 1a1.

The zone A2 is flat and has, substantially in its center, an opening 1b adapted to enable elastic deformation of the zone A2. More particularly, the opening 1b defines at least two anchor arms 1c and 1d, each having at least one outwardly projecting tooth 1c1, 1d1.

Advantageously, between the two zones A1 and A2, the body 1 has a central transition zone C adapted to withstand shear and flexion forces that can occur at the end of a bone. By way of non-limiting example, this median zone C can have a length of about 3.5 mm and a thickness of about 2 mm, for an overall implant length comprised between about 15 and 25 mm and a diameter of about 2 or 3 mm at the zone A1.

In the embodiment shown in FIG. 1, the two zones A1 and A2 are coaxial.

To solve the problem of adaptation to the shape of the implantation site, the anchor zones A1 and A2 can be offset by an angle α adapted to the geometry of the bone site. This angle α is comprised between about 1° and 30° and, advantageously, on the order of 10° when the implant is for foot arthrodesis (FIG. 5).

In this embodiment in which the two anchor zones are angularly offset, the bend is located so as to correspond substantially to the arthrodesis line of the bone parts being fused.

FIGS. 6 and 7 schematically show the positioning of the implant according to the invention between two bone parts O1 and O2. After suitable holes have been made in the bone by a rasp-type tool, the operator screws the thread 1a into the bone part O1 substantially up to the median zone C that serves as an abutment preventing the implant from sinking too deeply into the bone (FIG. 6). The operator then fits the second bone part O2 back onto the anchor arms 1d and 1c of the zone A2, and the anchor arms then spread and tighten by elasticity (FIG. 7).

The operative technique can be the following:

Drilling of the two holes with a conventional drill;

Preparation of the holes with a rasp for the flat side and a bone tap to form the inner screw thread on the cylindrical side;

Use of a screwdriver with a gripper end;

Screwing in the cylindrical side P1 for a PIP arthrodesis of the foot;

Fitting of the bone back onto the flat side of the implant.

The advantages are readily apparent from the description; in particular, it is to be emphasized and understood that the combination of the two anchor zones A1 and A2 of cylindrical and flat shape, respectively, significantly enhances anchoring and stability of the implant adapted to the geometry of the bone site and the material properties, namely, a resorptive material.

The invention claimed is:

1. An intramedullary implant for use between first and second bone parts, the implant comprising:
a first threaded end for anchoring to the first bone part;
a second end extending from the first end for anchoring to the second bone part, the second end having a longitudinal axis, a body portion, and a plurality of teeth projecting from the body portion, wherein at least a first tooth of the plurality of teeth is spaced from a second tooth of the plurality of teeth in a direction along the longitudinal axis of the second end, the first and second teeth extending from the body portion in a same direction, and at least the first tooth extending from the body portion in a different direction than a direction a third tooth of the plurality of teeth extends from the body portion.

2. The intramedullary implant of claim 1, wherein the first threaded end tapers in a direction away from the second end.

3. The intramedullary implant of claim 1, wherein the second end has an opening in a median portion therein, the opening allowing for elastic deformation of the second end.

4. The intramedullary implant of claim 3, wherein the opening defines at least two spreadable arms.

5. The intramedullary implant of claim 1, further comprising a central transition zone between the first and second ends, the central transition zone defined at the second end by an abutment at an edge of the second end, the abutment being transverse to a longitudinal axis of the first end adapted to prevent overinsertion of the implant into the second bone part.

6. The intramedullary implant of claim 5, wherein a face of the abutment defines a plane perpendicular to the longitudinal axis of the first end.

7. The intramedullary implant of claim 1, wherein a longitudinal axis through the first end is offset from the longitudinal axis of the second end by an angle less than 30 degrees.

8. The intramedullary implant of claim 7, wherein the offset is located at a position corresponding substantially to an arthrodesis line defined at the intersection of the first and second bone parts.

9. The intramedullary implant of claim 1, wherein the implant is made of resorptive material.

10. The intramedullary implant of claim 1, wherein the first and third teeth are positioned at the same axial location along the longitudinal axis of the second end.

11. The intramedullary implant of claim 1, wherein the body portion has opposing flat surfaces parallel to the longitudinal axis.

12. The intramedullary implant of claim 1, wherein a flat surface of the first tooth is coplanar with a flat surface of the second tooth.

13. The intramedullary implant of claim 1, wherein a cross-section of the body portion is non-circular.

14. The intramedullary implant of claim 1, wherein the first tooth, the second tooth, and the third tooth each include flat surfaces, the flat surfaces of the first tooth, the second tooth, and the third tooth defining planes parallel to each other.

15. An intramedullary implant for use between first and second bone parts, the implant comprising:
a first threaded end for anchoring to the first bone part;
a second end extending from the first end for anchoring to the second bone part and having a plurality of outwardly projecting teeth, at least a first tooth of the plurality of teeth spaced from a second tooth of the plurality of teeth in a direction along the longitudinal axis of the second end, and at least the first tooth extending in a different direction than a third tooth of the plurality of teeth, the second end having an opening in a median portion thereof.

16. The intramedullary implant of claim 15, further comprising a central transition zone between the first and second ends, the central transition zone defined at the second end by an abutment at an edge of the second end, the abutment being transverse to a longitudinal axis of the first end adapted to prevent overinsertion of the implant into the second bone part.

17. The intramedullary implant of claim 15, wherein the second end has a cross-section with opposing flat first and second surfaces when viewed in a direction perpendicular to a longitudinal axis thereof.

18. The intramedullary implant of claim 15, wherein a flat surface of the first tooth is coplanar with a flat surface of the second tooth.

\* \* \* \* \*